(12) United States Patent
Kloss et al.

(10) Patent No.: US 9,399,203 B2
(45) Date of Patent: Jul. 26, 2016

(54) DEVICE FOR AERATION, PARTICULARLY FOR MICROBIOLOGICAL FERMENTATION AND FOR CELL CULTIVATION

(75) Inventors: Andreas Kloss, Poing (DE); Hanspeter Tschamber, Schopfheim (DE)

(73) Assignee: MUT-Tschamber Misch und Trenntechnik GmbH, Wehr (DE)

( * ) Notice: Subject to any disclaimer, the term of this patent is extended or adjusted under 35 U.S.C. 154(b) by 1480 days.

(21) Appl. No.: 12/446,823

(22) PCT Filed: Oct. 25, 2007

(86) PCT No.: PCT/EP2007/009274
§ 371 (c)(1),
(2), (4) Date: Mar. 29, 2010

(87) PCT Pub. No.: WO2008/049617
PCT Pub. Date: May 2, 2008

(65) Prior Publication Data
US 2010/0178685 A1    Jul. 15, 2010

(30) Foreign Application Priority Data
Oct. 25, 2006 (CH) ........................... 1702/06

(51) Int. Cl.
*C12M 1/00* (2006.01)
*C12M 3/00* (2006.01)
(Continued)

(52) U.S. Cl.
CPC .............. *B01F 7/183* (2013.01); *B01F 3/04539* (2013.01); *C12M 27/04* (2013.01)

(58) Field of Classification Search
CPC ...... C12M 27/04; B01F 3/04539; B01F 7/183

USPC ..................... 435/243, 289.1; 366/102–107
See application file for complete search history.

(56) References Cited

U.S. PATENT DOCUMENTS

| 4,725,548 A | 2/1988 | Karrer |
| 4,836,826 A * | 6/1989 | Carter .............................. 464/29 |

(Continued)

FOREIGN PATENT DOCUMENTS

| DE | 10 2004 062 703 A1 * | 6/2006 | ................ B01F 7/16 |
| EP | 1473358 A2 * | 11/2004 | ............... C12M 1/06 |

(Continued)

OTHER PUBLICATIONS

Machine Translation of EP1 473 358 A2 (translated on Jan. 3, 2012).*
(Continued)

*Primary Examiner* — Michael Hobbs
(74) *Attorney, Agent, or Firm* — Brian Roffe

(57) ABSTRACT

A device for aeration, particularly for microbiological fermentation and for cell cultivation in a closed chamber. The device includes a sterilizable reactor (1) and a vertical stirring shaft (2) with numerous aeration and/or stirring elements (10) which are attached thereto and arranged in multiple levels vertically. The aeration elements (15) are constructed to create such an aeration of the liquid in the reactor that the gases are evenly introduced into the liquid as micro bubbles. The device also includes a recoil nozzles (20) connected to gas feed channels (11, connected to gas feed channels (11,12) connected to gas feed channels (11, 12, 14) for the purpose of driving the aeration and/or stirring elements (10) attached to the rotatably mounted stirring shaft (2). The result is a space-saving and absolutely hermetic construction of such a device.

21 Claims, 2 Drawing Sheets

(51) Int. Cl.
*B01F 7/18* (2006.01)
*B01F 3/04* (2006.01)
*C12M 1/04* (2006.01)

(56) References Cited

U.S. PATENT DOCUMENTS 5,045,470 A * 9/1991 Kloss .................... 435/297.2
5,779,996 A * 7/1998 Stormo .................... 422/227
6,270,061 B1 8/2001 Bouquet et al.

FOREIGN PATENT DOCUMENTS

| EP | 1479758 A2 * | 11/2004 | ............ C12M 1/06 |
| WO | WO 89/09814 * | 10/1989 | ............ C12M 3/00 |
| WO | WO 2007/038893 A1 * | 4/2007 | ............ B01F 11/00 |

OTHER PUBLICATIONS

Machine Translation of EP 1479758 A2. Translated Jan. 29, 2015.*

* cited by examiner

DEVICE FOR AERATION, PARTICULARLY FOR MICROBIOLOGICAL FERMENTATION AND FOR CELL CULTIVATION

FIELD OF THE INVENTION

The invention relates to a method and a device for aeration, particularly for microbiological fermentation and for cell cultivation in a closed chamber, wherein in a sterilizable reactor, a gas and/or air is injected in a metered fashion via aeration elements, and a vertical stirring shaft, having a number of aeration and/or stirring elements attached to the stirring shaft and arranged one over the other in multiple levels, is disposed in the reactor.

BACKGROUND OF THE INVENTION

A device of this type is known, for example, from EP-A-0 365 621. A vertical stirring shaft with numerous aeration and/or stirring elements arranged one over the other in multiple levels is disposed in a sterilizable reactor. The aeration elements and preferably also the stirring elements are hollow in form, connected to gas feed channels and provided with at least one gas-permeable part. With its one end the stirring shaft projects through the reactor wall and is driven by an electric motor disposed outside of the reactor. Since, for example, a cell culture bioreactor must be hermetically closed, the sealing of the stirring or drive shaft rotating in the fixed reactor poses a real problem.

OBJECTS AND SUMMARY OF THE INVENTION

The object which forms the basis of the present invention is to provide a method with optimised aeration of a liquid in the reactor and to simplify the structure of a device of the type specified at the start and to improve its sterilizing technology.

This object is achieved according to the invention by a method wherein aeration elements are designed such that they bring about aeration of the liquid in the reactor such that the gasses are introduced uniformly into the liquid as micro bubbles and by a device for implementing the method wherein the aeration elements each have an elongate hollow body with a gas-permeable insert disposed over approximately the whole length on the upper and/or lower side. The hollow body forming a respective aeration element is tubular in form, and each gas-permeable insert is made of a sintered metal, of ceramic or of a synthetic material. Further, the aeration elements distributed over the height of the reactor are provided with inserts which are provided either with surfaces of different sizes and/or however with different porosities dependently upon the hydrostatic pressure of the liquid to be fermented or cultivated in the reactor.

Further preferred embodiments of the method and the device according to the invention form the subject matter of the dependent claims.

With the method according to the invention the aeration elements are designed such that they can be of variable form dependently upon the oxygen requirements of the product creators. The gas bubbles must be introduced uniformly into the liquid as the smallest bubbles possible. These requirements are fulfilled by means of the aeration slots adapted to the surface area.

The device according to the invention is simple and inexpensive because all of the sealing problems relating to the rotating stirring shaft and the external atmosphere are dispensed with and a hermetically closed reactor chamber can be guaranteed without any great complexity. Moreover, the device can be space-saving in design because no external drive is required.

Aeration elements with inserts are provided distributed over the height of the reactor, and these enable a metered supply of gas.

BRIEF DESCRIPTION OF THE DRAWINGS

In the following the invention is described in greater detail by means of the drawings. These show as follows.

DETAILED DESCRIPTION OF THE INVENTION

Figure 1:
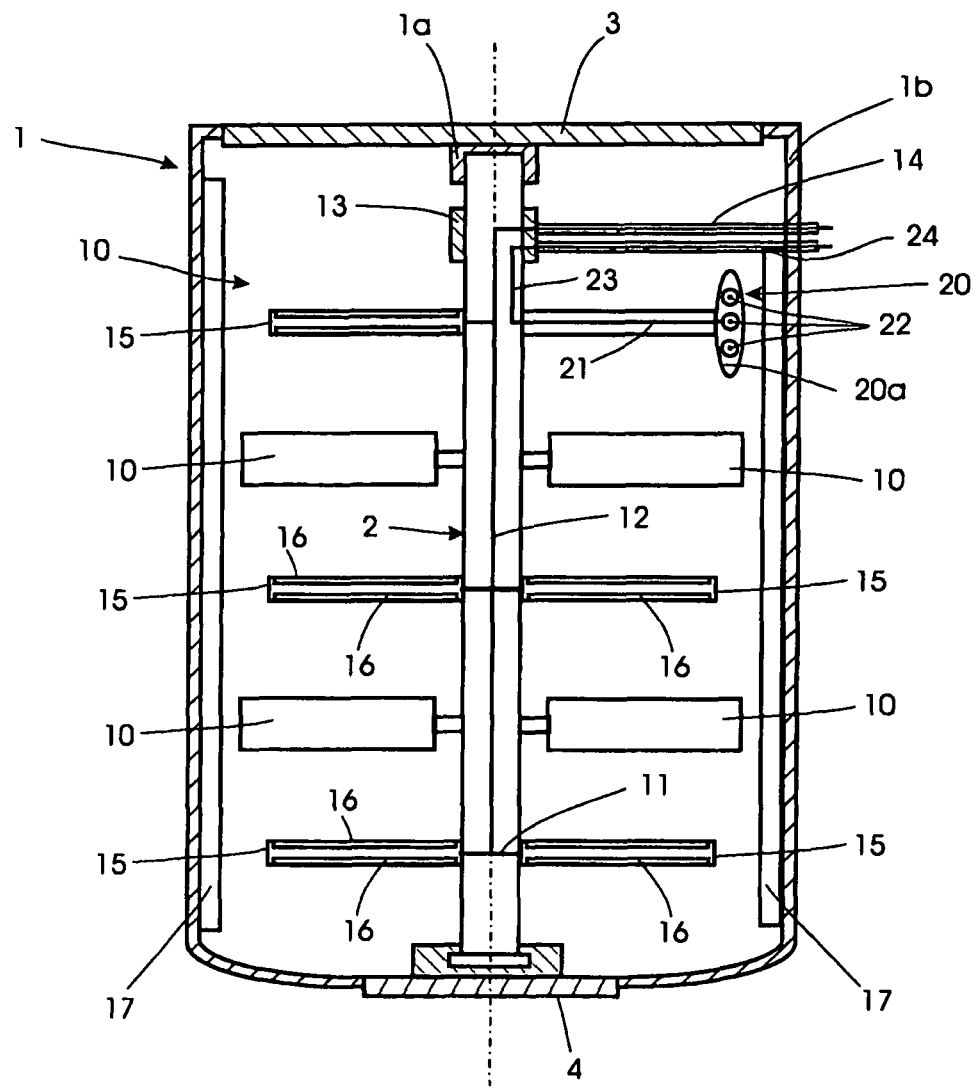
FIG. 1 a diagrammatic representation of a device according to the invention for aeration with aeration and/or stirring elements disposed one over the other in four levels.

FIG. 1 shows a reactor 1 which forms a bioreactor provided for microbiological fermentation and for cell cultivation. Disposed rotatably within the reactor 1 is a stirring shaft 2 which is held by its one end in a shaft suspension or mounting 3 and is mounted with the other end in a base mounting 4. With the exemplary embodiment shown the shaft suspension or mounting 3 is allocated to a reactor cover 1a.

Disposed one over the other in multiple levels on the stirring shaft 2 in the form of a hollow shaft are a number of radially extending aeration elements 15 and/or stirring elements 10, in this instance aeration elements 15 in three levels and stirring elements 10 in the two levels lying between. Moreover, chicane elements 17 preferably allocated to the inside of the reactor wall are provided which serve to prevent rotation of the liquid and occasionally bring about homogenisation with low rotation speeds of the stirring shaft 2.

With the method according to the invention the aeration elements 15 are formed such that they are held variably dependently in particular upon the oxygen requirement of the product formation occurring due to the aeration and that they bring about aeration of the liquid in the reactor such that the gases are introduced uniformly into the liquid as micro bubbles, preferably with a diameter of less then a millimeter. Moreover, homogeneous distribution of the bubbles in the liquid column should take place.

Figures 2, 3:
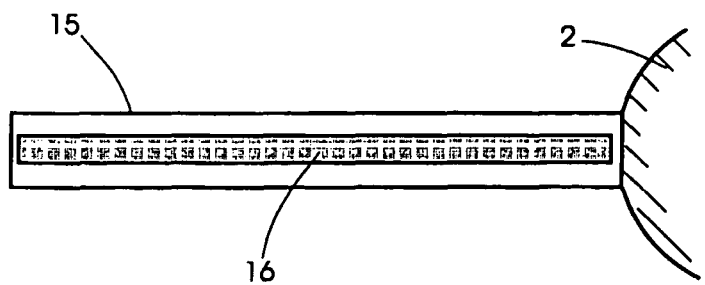
FIG. 2 an aeration element according to the invention according to FIG. 1, viewed from above.
FIG. 3 a cross-section through the aeration element according to FIG. 2.

According to FIG. 2 and FIG. 3 the aeration elements 15 respectively comprise an elongate hollow body with gas-permeable inserts 16 disposed over approximately the whole length on the upper and the lower side. The hollow body forming a respective aeration element 15 with a corresponding gas feed channel 11 is tubular in form here so that the gas to be injected is conveyed to the end of the hollow body. These gas-permeable inserts 16 are preferably made of a sintered metal, such as for example stainless steel. They could, however, also be made of ceramic or of a synthetic material.

According to the invention, these aeration elements 15 distributed over the height of the reactor 1 are provided with inserts 16 which are provided either with surfaces of different sizes or however with different porosities, and this is dependent particularly upon the oxygen requirement of the product creators. Moreover, the hydrostatic pressure of the liquid is to be taken into consideration. Therefore, with the aeration elements 15, in the lower region of the reactor 1 larger surfaces or greater porosity of the inserts 16 than in the upper region are to be provided. The aeration elements 15 are supplied with the gas by a gas feed channel 11, 12 passed through the stirring shaft 2.

The stirring elements 10 projecting radially away from the stirring shaft 2 are disposed on different levels. In principle they could also be equipped with inserts 16 and at the same time serve as aeration elements. With the latter the stirring effect for homogenisation of the reactor content is guaranteed, it being possible to choose a low rotation speed (5 to 100 r/min) since with the method in question dispersion of the gas bubbles is not necessary.

Furthermore, within the framework of the invention, in the upper region of the reactor 1 a drive component 20 is provided with a blade part 20a attached at the end and a separate gas and/or air feed 21 with which this stirring shaft 2 can be rotated. This blade part 20a has at least one, and if appropriate three recoil nozzles 22 which are substantially aligned in the circumferential direction of the stirrer shaft 2. The blade part 20a provided with the recoil nozzles 20 is respectively connected via the separate gas feed channel 21 to a vertical gas feed channel 23 passed through the rotating stirring shaft 2 and which in turn is connected via a conversion unit 13 to a gas feed line 24 securely fitted in a reactor wall 1b.

By means of this separate gas feed channel 24 gas from a compressed gas source can be introduced into the blade part 20a in such a quantity and under such a pressure that the gas passing out of the recoil nozzles 20 brings about propulsion of the whole stirrer, i.e. of all of the stirring and/or aeration elements 10, 15 connected in a rotationally fixed manner to the stirring shaft 2. The quantity of gas and the gas pressure required as impulse transmitters for the propulsion are achieved by the combination of the gas quantity regulation taking place on the outside in accordance with a corresponding nozzle cross-section.

Therefore, at least with bioreactors, which are provided for laboratory purposes or for smaller production units, the drive of the stirring shaft 2 provided with the stirring and/or aeration elements can only take place by means of the recoil nozzles 20 bringing about the propulsion, and the stirring shaft 2 does not need to be moved through the reactor wall to an external drive. It is located within the reactor 1, held in the shaft suspension 3 and passed into the base mounting 4, for example a TEFLON® mounting. The bioreactor is hermetically closed. The preferably welded in gas feed lines 14, 24 opening out into the reactor 1 and securely fitted in the reactor wall or in the reactor cladding 1b do not form any risk of an unsealed point. Gas feed line 14, as shown in FIG. 1, connects to the gas feed channel 12 which in turns connects to the gas feed channels 11 that leads to the aeration elements 15.

For very large production units, if need be an additional passage-free magnetic drive could be provided, i.e. by means of a magnetic coupling known in its own right (instead of the base mounting 4) the stirring shaft 2 could additionally be driven by a motor lying outside of the reactor 1 without having to project through the reactor wall here.

Figure 4:
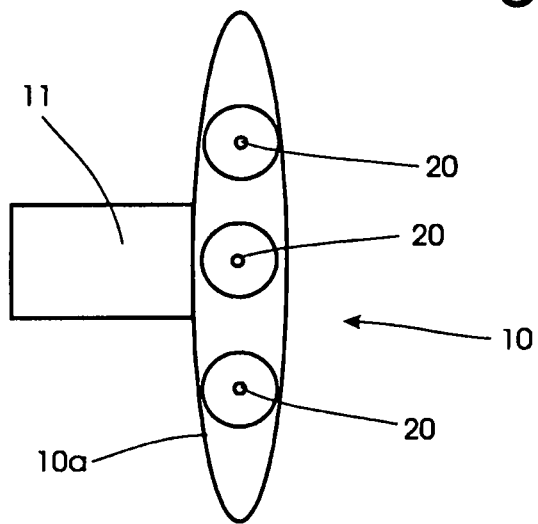
FIG. 4 a side view of an exemplary embodiment of an aeration and/or stirring element according to the invention.
Figure 5:
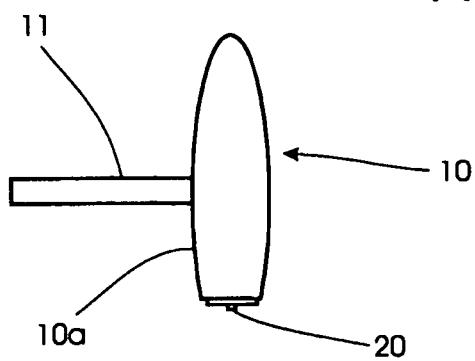
FIG. 5 a top view of the aeration and/or stirring element according to FIG. 4.

Advantageously, the blade parts 10a have an aerodynamic form with optimised fluid technology, as indicated in FIGS. 4 and 5. This facilitates the rotary movement of the stirring elements 10.

Advantageously, the same gas can be used for the propulsion as is also provided for aerating the fermentation slurry, e.g. sterile air, pure oxygen or an oxygen/nitrogen mixture.

The device according to the invention for aeration, particularly for microbiological fermentation and for cell cultivation in a closed chamber, is simple and inexpensive because all of the sealing problems relating to the rotating stirring shaft are dispensed with, and a hermetically closed reactor chamber can be guaranteed without any great complexity. The device can be space-saving in design because an external drive is not required.

Of course when using a larger reactor a number of these recoil nozzles according to the invention could be used. The number of aeration and stirring elements can also be varied depending on the size of the reactor. In principle the inserts with the aeration elements could also be aligned at an angle downwardly, upwardly or horizontally.

The invention claimed is:

1. A device for aeration, comprising:
a hermetically sealed reactor defining an interior space, said hermetically sealed reactor having a base at a bottom, a cover at a top and a side wall extending between said base and said cover;
a rotatable stirring shaft arranged in said interior space and spaced apart from said side wall such that an interior reactor space is defined between a side surface of said stirring shaft and said side wall;
projecting elements that project from said stirring shaft;
at least one first gas feed channel arranged in connection with said stirring shaft and coupled to at least one of said projecting elements to enable gas to flow through said at least one first gas feed channel to said at least one projecting element;
at least one second gas feed channel arranged in connection with said stirring shaft and separate from said at least one first gas feed channel;
a gas feed system having a portion connected at a first end to said side surface of said stirring shaft and connected at a second, opposite end to said side wall of said hermetically sealed reactor, said portion of said gas feed system extending through said interior reactor space between said stirring shaft and said side wall, said gas feed system being coupled to said first and second gas feed channels to enable gas to flow through said gas feed system to said first and second gas feed channels; and
a propulsion drive component arranged in said interior space of said hermetically sealed reactor for rotating said stirring shaft and thus said projecting elements projecting therefrom, said second gas feed channel being coupled to said drive component to enable gas to flow through said second gas feed channel to said drive component and thereby enable said drive component to rotate said stirring shaft when gas is directed out of said drive component;
a shaft suspension or mounting arranged on said cover and rotatably retaining an upper end of said stirring shaft such that said stirring shaft operatively rotates relative to said shaft suspension or mounting while being retained by said shaft suspension or mounting; and
a base mounting extending upward from a lower surface of said base into said interior space of said hermetically sealed reactor, a lower end of said stirring shaft being rotatably retained in said base mounting such that said stirring shaft operatively rotates relative to said base mounting while being retained in said base mounting, said stirring shaft being retained between said shaft suspension or mounting and said base mounting such that said stirring shaft is entirely in said interior space of said hermetically sealed reactor.

2. The device according to claim 1, wherein said drive component comprises:
- a blade part projecting outward from said stirring shaft; and
- at least one recoil nozzle arranged at an outward end of said blade part and from which gas is directed into said interior space of said reactor, said second gas feed channel being coupled to said at least one recoil nozzle to enable gas to flow through said second gas feed channel to said at least one recoil nozzle.

3. The device according to claim 2, wherein said blade part has an aerodynamic outer form facilitating rotary movement of said projecting elements.

4. The device according to claim 1, wherein said gas feed system includes a third gas feed channel through which gas for propulsion of said drive component is introduced into said second gas feed channel in a required quantity and under a pre-specified pressure from a compressed gas source.

5. The device according to claim 4, wherein said drive component comprises:
- a blade part projecting from said stirring shaft; and
- at least one recoil nozzle arranged at an end of said blade part and through which gas is directed into said interior space of said reactor, said second gas feed channel being coupled to said at least one recoil nozzle to enable gas to flow through said second gas feed channel to said at least one recoil nozzle,
- said gas feed system comprising a conversion unit partly interposed between said second gas feed channel and said third gas feed channel, said conversion unit enabling rotation of said stirring shaft relative to said third gas feed channel,
- said third gas feed channel extending in a radial direction from said stirring shaft and at least partly in said portion of said gas feed system extending through said interior reactor space between said stirring shaft and said side wall.

6. The device according to claim 1, wherein said projecting elements comprise at least one aeration element.

7. The device according to claim 6, wherein each of said at least one aeration element is configured to inject the gas and/or air into said interior space of said reactor in a metered fashion.

8. The device according to claim 6, wherein each of said at least one aeration element is configured to introduce gas into said interior space of said reactor uniformly as micro bubbles to thereby cause aeration of liquid when present in said interior space of said reactor.

9. The device according to claim 1, wherein said projecting elements comprise stirring elements.

10. The device according to claim 1, wherein said projecting elements comprise aeration elements and stirring elements.

11. The device according to claim 1, wherein said projecting elements are attached to said stirring shaft.

12. The device according to claim 1, wherein said projecting elements are arranged one over another in multiple levels along said stirring shaft.

13. The device according to claim 1, wherein said stirring shaft is vertically oriented in said interior space of said reactor and a portion of each of said first and second gas feed channels extends vertically along said stirring shaft.

14. The device according to claim 1, wherein a portion of each of said first and second gas feed channels is arranged within said stirring shaft.

15. The device according to claim 1, wherein said portion of said gas feed system extending through said interior reactor space between said stirring shaft and said side wall is secured to said peripheral wall of said reactor.

16. The device according to claim 1, wherein said portion of said gas feed system extending through said interior reactor space between said stirring shaft and said side wall is securely fitted in said peripheral wall of said reactor.

17. The device according to claim 1, wherein said projecting elements comprise at least one aeration element configured to introduce gas into said interior space of said reactor, and said gas feed system comprises:
- a third gas feed channel through which gas for propulsion of said drive component is introduced into said second gas feed channel; and
- a fourth gas feed channel, separate from said third gas feed channel, through which gas is introduced into said at least one first gas feed channel to be provided to said at least one aeration element,
- said third and fourth gas feed channels being situated at least partly in said portion of said gas feed system extending through said interior reactor space between said stirring shaft and said side wall.

18. The device according to claim 1, wherein said drive component comprises at least one recoil nozzle from which gas is directed into said interior space of said reactor,
- said second gas feed channel being coupled to said at least one recoil nozzle to enable gas to flow through said second gas feed channel to said at least one recoil nozzle,
- each of said at least one recoil nozzle being aligned in a circumferential direction of said stirring shaft.

19. The device according to claim 1, wherein said portion of said gas feed system extends radially outward from said stirring shaft in a direction toward said side wall of said reactor.

20. The device according to claim 1, wherein said first and second gas channels cooperate with said gas feed system such that said first and second gas feed channels only receive gas that flows through said portion of said gas feed system that extends through said interior reactor space between said stirring shaft and said side wall.

21. The device according to claim 1, wherein said base mounting is a separate unit from said base, the lower end of said stirring shaft is passed into said base mounting and said base mounting is in contact with said stirring shaft.

* * * * *